US00PP25093P3

(12) United States Plant Patent
Zaiger et al.

(10) Patent No.: US PP25,093 P3
(45) Date of Patent: Nov. 25, 2014

(54) PEACH TREE NAMED 'SNOW LADY ROSE'

(50) Latin Name: *Prunus persica*
Varietal Denomination: Snow Lady Rose

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 0 days.

(21) Appl. No.: 13/986,286

(22) Filed: Apr. 19, 2013

(65) Prior Publication Data

US 2014/0317796 P1 Oct. 23, 2014

(51) Int. Cl.
*A01H 5/08* (2006.01)

(52) U.S. Cl.
USPC ..... Plt./195

(58) Field of Classification Search
CPC ..... A01H 5/0868
USPC ..... Plt./195
See application file for complete search history.

(56) References Cited

PUBLICATIONS

UPOV Record Detail Peach 'Snow Lady' obtained from PLUTO database Jun. 6, 2014.*

* cited by examiner

*Primary Examiner* — June Hwu
*Assistant Examiner* — Keith Robinson

(57) ABSTRACT

A new and distinct variety of peach tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Tree with vigorous, upright growth.
2. Having a low winter chilling requirement of approximately 300 hours at or below 45° F.
3. Regular and productive bearer of large size fruit.
4. Fruit with a mild, sweet, low acid flavor and very good flavor and eating quality.
5. Fruit with a high degree of attractive red skin color.
6. Fruit with good storage and shipping quality.

1 Drawing Sheet

Botanical designation: *Prunus persica.*
Variety denomination: 'Snow Lady Rose'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of peach tree was originated and asexually reproduced by us in our experimental orchard located near Modesto, Stanislaus County, Calif.

PRIOR VARIETIES

Among the existing varieties of peach trees, which are known to us, and mentioned herein, 'Zee Pride' Peach (U.S. Plant Pat. No. 22,606), 'Snow Angel' Peach (U.S. Plant Pat. No. 18,750) and our proprietary non-patented peach seedlings '42ZG640' and '204LK484'.

STATEMENT REGARDING FEDERALLY SPONSORED RESEARCH AND DEVELOPMENT

Not applicable.

ORIGIN OF THE VARIETY

The new and distinct variety of peach tree (*Prunus persica*) was developed by us in our experimental orchard located near Modesto, Calif. from seed of our open pollinated proprietary non-patented peach seedling with the field identification number '42ZG460'. The seed parent (42ZG460) originated as a first generation cross between our proprietary non-patented peach seedling '204LK484' and 'Zee Pride' Peach (U.S. Plant Pat. No. 22,606). A large number of these open pollinated peach seedlings were grown and budded to older trees of 'Nemaguard' Rootstock (non-patented), to accelerate rapid fruit production. Under close and careful observation we recognized the desirable tree and fruit characteristics of the present seedling and selected it in 2007 for additional asexual propagation and commercialization.

ASEXUAL REPRODUCTION OF THE VARIETY

Asexual reproduction of the new and distinct variety of peach tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new variety of peach tree (*Prunus persica*) is of large size, vigorous, upright growth and a productive and regular bearer of large size, white flesh, clingstone fruit with mild, sweet, low acid flavor and very good eating quality. The fruit is further characterized by having an attractive red skin color with good handling and storage ability. In comparison to its seed parent (42ZG460) peach (non-patented) the fruit of the new variety has firmer flesh and is approximately 15 days earlier in maturity. In comparison to the commercial peach variety 'Snow Angel' (U.S. Plant Pat. No. 18,750) the fruit of the new variety is larger in size and is approximately 10 days later in maturity.

DESCRIPTION OF THE PHOTOGRAPH

The accompanying color photographic illustration shows typical specimens of the foliage and fruit of the present new peach variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 7 year old tree and the colors are as nearly true as is reasonably possible in a color representation of this type.

DESCRIPTION OF THE VARIETY

The following is a detailed botanical description of the new variety of peach tree, its flowers, foliage and fruit, as based on observations of 7 year old specimens grown near Modesto, Calif., with color in accordance with Munsell Book of Color published in 1958.

Tree:

*Size*.—Large, usually pruned to 3 to 3.5 meters in height and width for economical harvesting of fruit, varies with different cultural practices.

*Vigor*.—Vigorous, growth of 1.5 to 2 meters in height the first growing season. Varies with soil type, fertility of soil and climatic conditions.

*Form*.—Upright, usually pruned to vase shape.

*Branching habit*.—Upright, crotch angle approximately 35°, increases with heavy crop load.

*Productivity*.—Productive, thinning and spacing of fruit necessary for desired market size. Fruit set varies with climatic conditions during bloom time.

*Bearer*.—Regular, adequate fruit set 5 consecutive years. No alternate bearing observed.

*Fertility*.—Self-fertile.

*Density*.—Medium dense, usually pruned to vase shape to allow more sunlight to center of tree to enhance fruit color and health of fruit wood.

*Hardiness*.—Hardy in all stone fruit growing areas of California. Tree grown in USDA Hardiness Zone 9. Winter chilling requirement approximately 300 hours at or below 45° F.

Trunk:

*Size*.—Large. Average circumference of 56.5 cm at 27.9 cm above ground on a 7 year old tree.

*Stocky*.—Medium stocky.

*Texture*.—Medium shaggy, roughness increases with age.

*Color*.—Varies from 2.5Y 4/4 to 5Y 4/2.

Branches:

*Size*.—Medium. Average circumference 13.8 cm at 1.2 meters above ground. Crotch angle approximately 35°, increases with crop load.

*Surface texture*.—New growth relatively smooth. Mature growth medium rough, roughness increases with age.

*Lenticels*.—Average number 23 in a 25.8 sq cm area. Average length 3.8 mm. Average width 2.1 mm. Color varies from 10YR 5/6 to 10YR 5/10.

*Color*.—New growth varies from 2.5GY 6/6 to 5GY 6/6. Mature growth varies from 2.5Y 5/4 to 2.5Y 3/4, varies with age of growth.

Leaves:

*Size*.—Large. Average length 136.2 mm. Average width 47.7 mm.

*Form*.—Lanceolate.

*Apex*.—Acuminate.

*Base*.—Cuneate.

*Margin*.—Serrulate.

*Thickness*.—Medium.

*Surface texture*.—Upper surface relatively smooth, slight indentations over midrib and leaf veins. Lower surface relatively smooth, except for small ridges created by midrib and pinnate venation. Both upper and lower surfaces glabrous.

*Petiole*.—Average length 9.6 mm. Average width 1.6 mm. Longitudinally grooved. Surface glabrous. Color varies from 5GY 5/6 to 5GY 4/6.

*Glands*.—Type — reniform. Size — medium to large. Average length 1.4 mm. Average diameter 1.0 mm. Number varies from 2 to 4, average number 3. Located primarily on the base of the leaf blade and the upper portion of the petiole. Color varies from 2.5GY 6/6 to 5GY 5/6.

*Stipules*.—Average number 2. Average length 7.7 mm. Edges — pectinate. Color varies from 2.5GY 7/6 to 2.5GY 6/6.

*Color*.—Upper surface varies from 7.5GY 3/4 to 7.5GY 3/6. Lower surface varies from 7.5GY 4/4 to 10GY 4/6. Midvein color varies from 2.5GY 6/6 to 5GY 6/6.

Flower buds:

*Size*.—Large. Average length 18.0 mm. Average diameter 10.2 mm.

*Hardiness*.—Hardy with respect to California winters.

*Density*.—Dense.

*Form*.—Conical, becoming elongated just before opening.

*Pedicel*.—Average length 4.9 mm. Average width 1.2 mm. Color varies from 2.5GY 6/6 to 5GY 6/6.

*Color*.—Varies from 5RP 7/8 to 7.5RP 6/10.

Flowers:

*Blooming period*.—Date of First Bloom Feb. 13, 2012. Date of Petal Fall Feb. 23, 2012, varies slightly with climatic conditions.

*Size*.—Large, showy. Average height 22.2 mm. Average diameter 39.4 mm.

*Petals*.—Normally 5, alternately arranged to sepals. Size — large. Average length 21.6 mm.. Average width 21.1 mm. Form — orbicular, narrowing at point of attachment. Arrangement — overlapping. Margin — sinuate. Color varies from 5RP 8/4 to 5RP 8/6, fades with age of flower. Both upper and lower surfaces glabrous.

*Sepals*.—Normally 5, alternately arranged to petals. Size — large. Average length 7.1 mm. Average width 6.5 mm. Shape — ovate, apex rounded. Margin — entire. Color — upper surface varies from 2.5GY 4/6 to 2.5R 3/4. Lower surface varies from 2.5R 3/2 to 2.5R 2/4. Upper surface glabrous, lower surface pubescent.

*Stamens*.—Average number per flower 38. Average filament length 16.9 mm. On average, the stamens are below the height of the petals. Filament color varies from N 9.5/ (white) to 5RP 6/6. Anther color varies from 5Y 8/8 to 7.5R 4/10.

*Pollen*.—Self-fertile. Color varies from 5Y 8/10 to 5Y 7/10.

*Pistil*.—Number — normally one. Surface pubescent. Average length 19.8 mm. Position of stigma an average of 2.9 mm below anthers. Color varies from 10Y 8/4 to 2.5GY 8/4.

*Fragrance*.—Wanting.

*Color*.—Varies from 5RP 8/4 to 5RP 7/6.

*Number flowers per flower bud*.—Normally one.

*Pedicel*.—Average length 5.1 mm. Average width 1.2 mm. Color varies from 2.5GY 5/8 to 5GY 5/6.

Fruit:

*Maturity when described*.—Firm ripe and ready for consumption.

*Date of first picking*.—May 19, 2012.

*Date of last picking*.—May 26, 2012, varies slightly with climatic conditions.

*Size*.—Large. Average diameter axially 61.6 mm. Average transversely in suture plane 71.3 mm. Average weight 187.4 grams, varies slightly with fertility of the soil, amount of thinning and climatic conditions.

*Form*.—Globose.

*Suture*.—Nearly smooth, extends from base to apex.

*Ventral surface*.—Nearly smooth.

*Apex*.—Retuse.

*Base*.—Retuse.

*Stem cavity*.—Rounded to slightly elongated in the suture plane. Average depth 7.4 mm. Average diameter 13.9 mm.

Stem:

*Size*.—Small. Average length 10.5 mm. Average diameter 2.8 mm.

*Color*.—Varies from 2.5GY 6/6 to 2.5GY 5/6.

Flesh:

*Ripens*.—Evenly.

*Texture*.—Firm and meaty.

*Fibers*.—Few, small, tender.

*Firmness*.—Good, comparable to other commercial varieties.

*Aroma*.—Moderate.

*Amydgalin*.—Undetected.

*Eating quality*.—Very good.

*Flavor*.—Very good, a mild, sweet, low acid flavor.

*Juice*.—Moderate amount, enhances flavor.

*Acidity*.—Not available.

*Brix*.—Average Brix 12.0°, varies slightly with amount of fruit per tree and climatic conditions.

*Pit cavity*.—Average length 32.0 mm. Average width 29.8 mm. Average depth 13.0 mm. Color varies from 7.5Y 8.5/4 to 10Y 8.5/2

*Color*.—Varies from 7.5Y 8.5/2 to 10Y 8.5/2. .

Skin:

*Thickness*.—Medium.

*Surface*.—Smooth.

*Pubescence*.—Moderate amount, very short.

*Tendency to crack*.—None.

*Color*.—Ground color varies from 2.5Y 9/2 to 5Y 8.5/2. Overspread with 5R 4/10 to 7.5R 3/12.

*Tenacity*.—Tenacious to flesh.

*Astringency*.—Undetected.

Stone:

*Type*.—Clingstone, strong adherence.

*Size*.—Large. Average length 30.6 mm. Average width 27.5 mm. Average thickness 23.1 mm.

*Form*.—Ovoid.

*Base*.—Flat.

*Apex*.—Rounded.

*Surface*.—Pitted throughout, pits vary from round to elongated.

*Sides*.—Unequal, one side extending further from the suture plane.

*Ridges*.—Relatively smooth, extending from base to apex.

*Tendency to split*.—Slight.

*Color*.—Varies from 10YR 8/4 to 10YR 6/4 when dry.

Kernel:

*Size*.—Medium to large. Average length 16.7 mm. Average width 12.3 mm. Average depth 7.2 mm.

*Form*.—Ovoid.

*Viability*.—Non-viable, incomplete embryo development.

*Skin color*.—Varies from 7.5Y 9/4 to 10Y 9/2.

Use:

*Dessert*.—Market — local and long distance.

Keeping quality: Good, held firm in cold storage for 2 weeks at 38° to 42° F. without internal breakdown of flesh or appreciable loss of flavor.

Shipping quality: Good, minimal skin scarring or flesh bruising during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program. No atypical resistances/susceptibilities have been noted under normal cultural practices. The present new variety of peach tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of peach tree, substantially as illustrated and described.

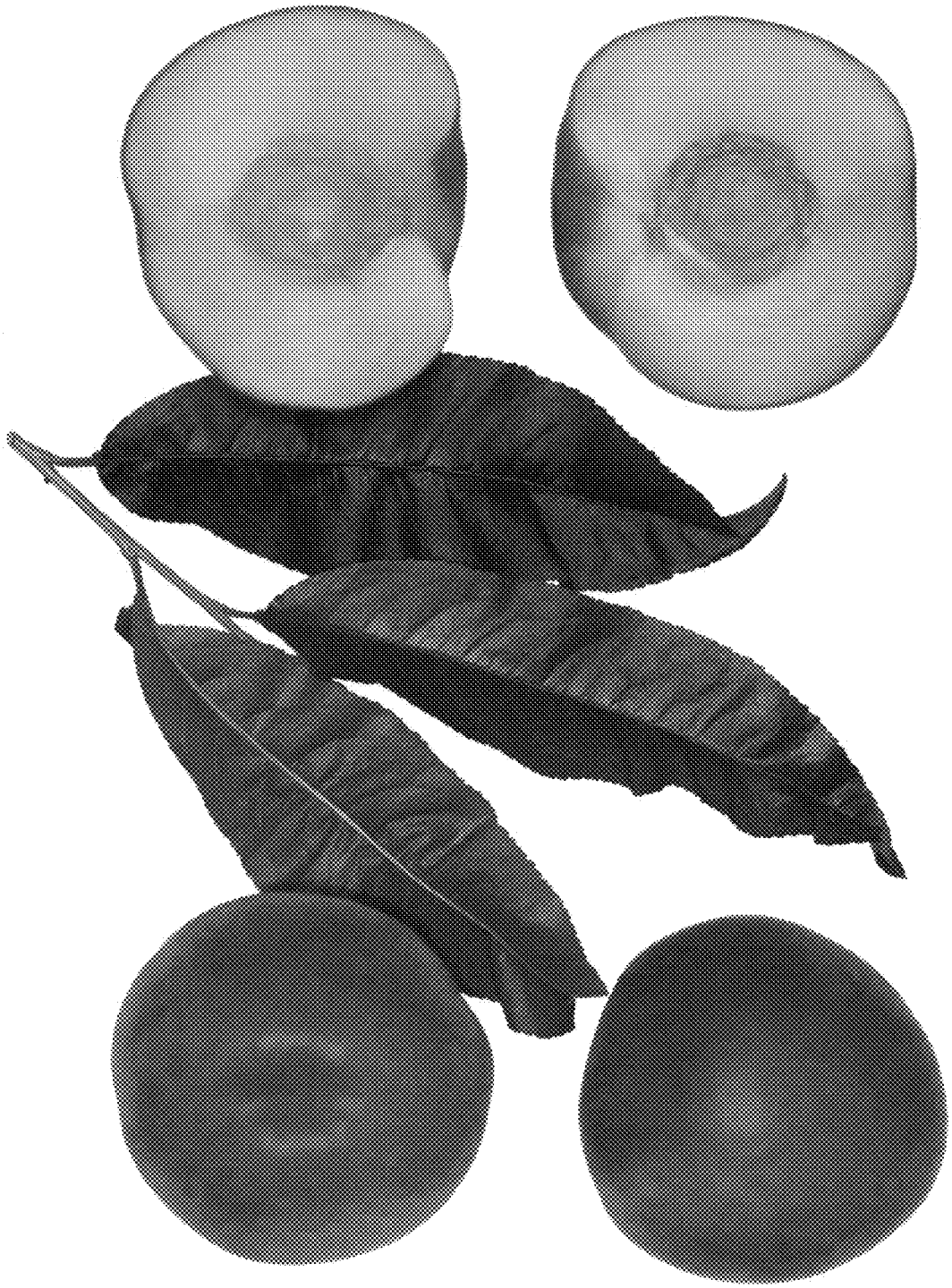

* * * * *